US00PP34543P2

(12) United States Plant Patent
Kraan

(10) Patent No.: US PP34,543 P2
(45) Date of Patent: Sep. 6, 2022

(54) ***HYDRANGEA* PLANT NAMED 'BOKOPIAV'**

(50) Latin Name: *Hydrangea paniculata*
Varietal Denomination: Bokopiav

(71) Applicants: Boot & Co Boomkwekerijen bv, Boskoop (NL); Kolster BV, Boskoop (NL)

(72) Inventor: Kees Jan Kraan, Alphen aan den Rijn (NL)

(73) Assignees: BOOT & CO BOOMKWEKERIJEN B.V., Boskoop (NL), part interest; KOLSTER B.V., Boskoop (NL), part interest ( * ) Notice: Subject to any disclaimer, the term of this patent is extended or adjusted under 35 U.S.C. 154(b) by 0 days.

(21) Appl. No.: 17/574,704

(22) Filed: Jan. 13, 2022

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea paniculata* named 'Bokopiav' that is characterized by its vigorous growth habit, its strong and healthy foliage that is maintained during flowering, its thick and strong branches, its ovate to conical shaped inflorescences, its inflorescences that consist of fertile and predominately sterile flowers, its sterile flowers with sepals that are green-white in color when opening, white in color at maturity that change to pink-purple in color, and its flowering that commences in mid-July.

2 Drawing Sheets

Genus/species: *Hydrangea paniculata.*
Varietal denomination: 'Bokopiav'.

BACKGROUND OF THE INVENTION

The present invention relates to a new and distinct cultivar of *Hydrangea paniculata* and will be referred to hereafter by its cultivar name, 'Bokopiav'. 'Bokopiav' represents a new panicle type *Hydrangea*, a deciduous shrub grown for landscape use and for use as a potted plant.

The new cultivar of *Hydrangea* arose from a breeding program conducted by the Inventor in Boskoop, The Netherlands with the goal of developing *Hydrangea* plants with dense and compact plant habits and inflorescences that are dense and have unique shapes. 'Bokopiav' originated as a seedling that arose from seed planted from open pollination of *Hydrangea paniculata* 'DVPPinky' (U.S. Plant Pat. No. 16,166) in July of 2010. 'Bokopiav' was selected as a single unique plant in September of 2020 from amongst the resulting seedlings.

Asexual propagation of the new cultivar was first accomplished by the Inventor by softwood stem cuttings in July of 2018 in Boskoop, The Netherlands. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish in 'Bokopiav' as a unique cultivar of *Hydrangea.*

1. 'Bokopiav' exhibits a vigorous growth habit.

2. 'Bokopiav' exhibits strong and healthy foliage that is maintained during flowering.
3. 'Bokopiav' exhibits thick and strong branches.
4. 'Bokopiav' exhibits ovate to conical shaped inflorescences.
5. 'Bokopiav' exhibits inflorescences that consist of fertile and predominately sterile flowers.
6. 'Bokopiav' exhibits sterile flowers with sepals that are green-white in color when opening, white in color at maturity that change to pink-purple in color.
7. 'Bokopiav' exhibits flowering that commences in mid-July.

The seed parent of 'Bokopiav', differs from 'Bokopiav' in having a shorter plant height, narrow conical shaped inflorescences, less sterile flowers per inflorescence, and sterile flower sepals that change to a deep pink-red color. 'Bokopiav' can be most closely be compared to *Hydrangea paniculata* cultivars 'HPOPR013' (U.S. Plant Pat. No. 27,472) and 'Bokraflame' (U.S. Plant Pat. No. 22,111). 'HPOPR013' is similar to 'Bokopiav' in overall plant and inflorescence shape. 'HPOPR013' differs from 'Bokopiav' in having a shorter plant height, narrow conical shaped inflorescences, less sterile flowers per inflorescence, and sterile flower sepals that change to a deep pink-red color. 'Bokraflame' is similar to 'Bokopiav' in overall plant shape. 'Bokraflame' differs from 'Bokopiav' in having a shorter plant size, thinner and weaker branches, inflorescences that are smaller in size and broadly ovate to very broadly ovate in shape, and sterile flower sepals that change to a red color.

BRIEF DESCRIPTION OF THE DRAWINGS

The accompanying colored photographs illustrates the overall appearance and distinct characteristics of a four year-old plant of the 'Bokopiav', as field grown outdoors in Boskoop, The Netherlands.

The photograph in FIG. 1 provides a side view of a plant of 'Bokopiav' in bloom.

Figure 1:
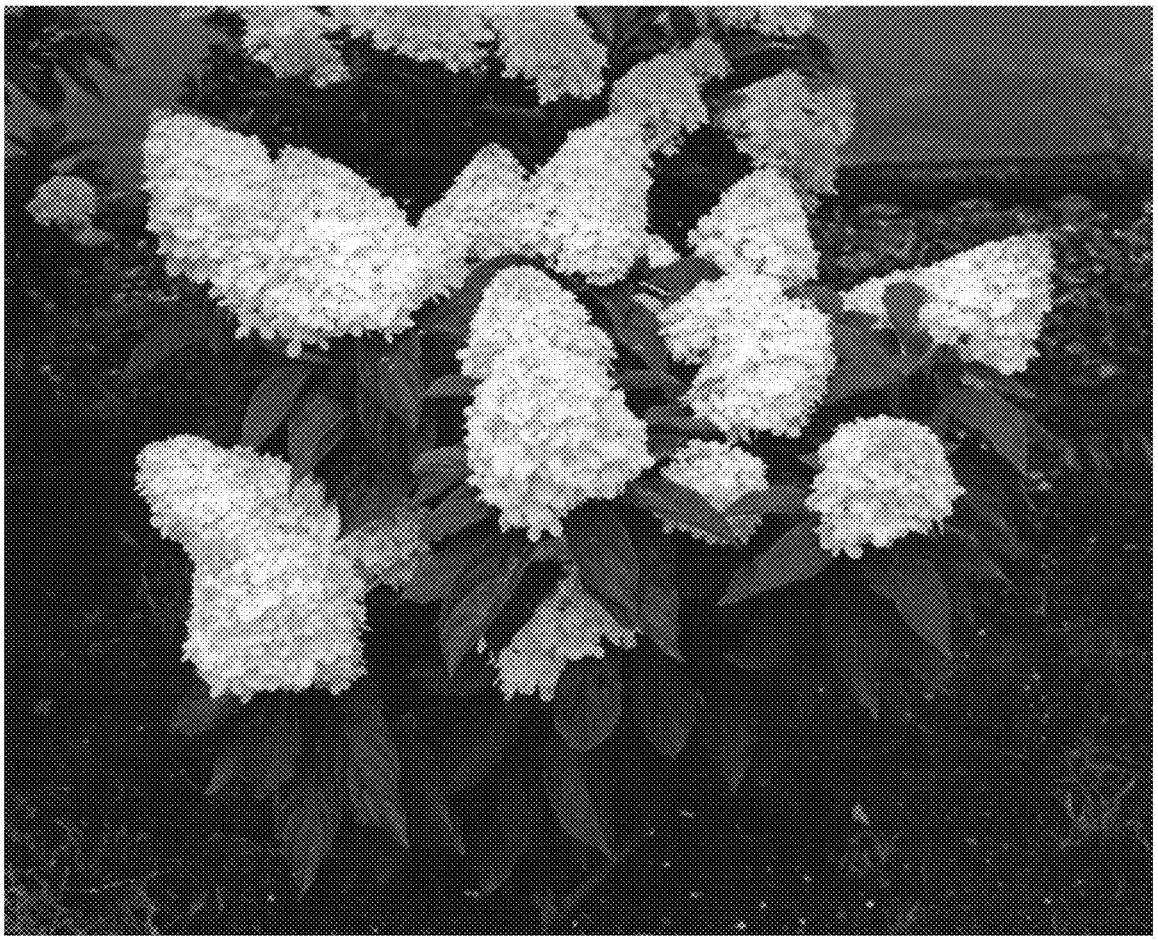
Figure 2:
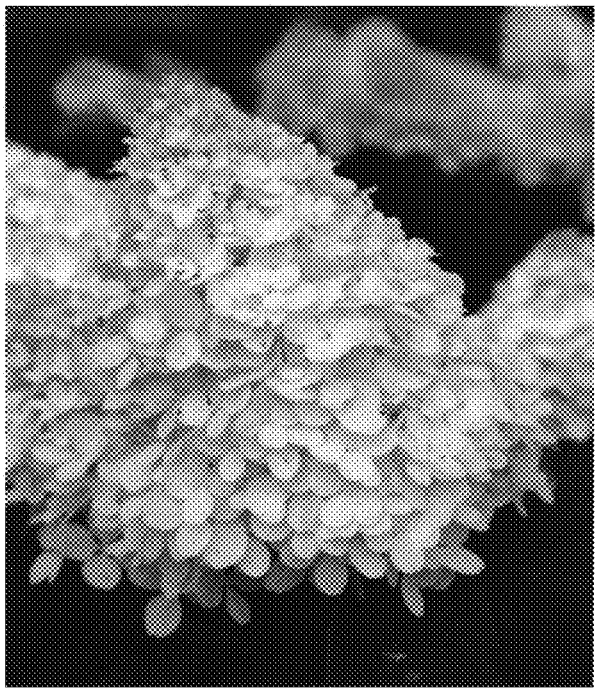

The photograph in FIG. 2 provides a close-up view of an inflorescence of 'Bokopiav'.

Figure 3:
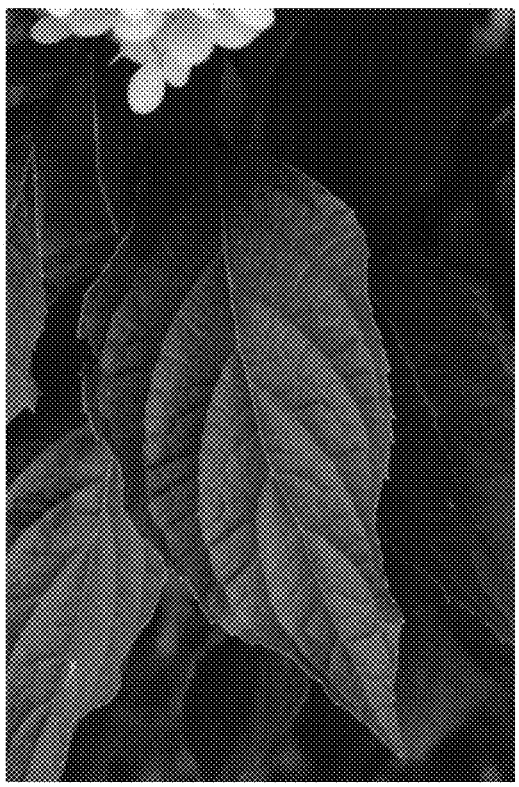

The photograph in FIG. 3 provides a close-up view of the foliage of 'Bokopiav'.

The colors in the photographs may differ slightly from the color values cited in the detailed botanical description, which accurately describe the colors of the new *Hydrangea*.

BOTANICAL DESCRIPTION OF THE PLANT

The following is a detailed description of the new cultivar as observed on 4 year-old plants as field grown outdoors in Boskoop, the Netherlands. Phenotypic differences may be observed with variations in environmental, climatic, and cultural conditions. The color determination is in accordance with The 2015 Colour Chart of The Royal Horticultural Society, London, England, except where general color terms of ordinary dictionary significance are used.

General description:

*Blooming period.*—Approximately 6 weeks from mid-July into early fall in The Netherlands.

*Plant type.*—Deciduous flowering shrub, panicle type *Hydrangea*.

*Plant habit.*—Broadly spreading, upright.

*Height and spread.*—Reaches 2 m in height and 1.5 m in spread as a mature plant in the landscape.

*Hardiness.*—At least in U.S.D.A. Zones 5 to 9.

*Diseases and pests.*—No susceptibility or resistance to diseases or pests has been observed.

*Root description.*—Fibrous and fine roots.

*Propagation.*—Softwood stem cuttings.

*Root development.*—An average of 30 days for root initiation with a young rooted plant produced in an average of 3 months.

*Growth rate.*—Moderate to vigorous.

Stem description:

*Stem shape.*—Rounded.

*Stem color.*—Young and mature; 200C, base strongly tinged 187B and 187C, older bark 197B to 197C, N199B and 200C, no fasciation observed.

*Stem size.*—Average of 27.6 cm in length and 5 mm in diameter.

*Stem surface.*—Young stems; sparsely to moderately covered with short adpressed hairs, 0.5 mm in length, matching surface color, sparsely to moderately covered with lenticels, 1 mm in length, 0.5 mm in width, 164B in color, mature stems glabrous.

*Stem aspect.*—Spreading upright, average angle 55° (soil level=0°).

*Internode length.*—Average of 3.7 cm.

*Branching.*—An average of 27 lateral branches, strong in strength.

Foliage description:

*Leaf shape.*—Elliptic to ovate.

*Leaf division.*—Simple.

*Leaf size.*—Average of 13.9 cm in length and 7.2 cm in width.

*Leaf base.*—Short attenuate.

*Leaf apex.*—Apiculate to acute.

*Leaf venation.*—Pinnate, color upper surface; 147C towards the base, color lower surface; a blend of 148D and 150D, tinged 176B.

*Leaf margins.*—Serrated, not lobed.

*Leaf attachment.*—Petiolate.

*Leaf arrangement.*—Opposite or in whorls of three.

*Leaf surface.*—Both surfaces dull, upper surface pubescence on main vein 0.3 mm in length, matching surface color, lower surface pubescence on main vein 0.4 mm in length, matching surface color.

*Leaf color.*—Young leaves upper surface; 137B and 143A, young leaves lower surface; 146B, mature and fall leaves upper surface; NN137B, mature and fall leaves lower surface; 146A to 146B.

*Petioles.*—Average of 2.3 cm in length and 3 mm in diameter, upper surface slightly glossy, moderately covered with pubescence, 0.3 mm in length, matches surface color, lower surface matte to very slightly glossy, very sparsely covered with pubescence 0.3 mm in length, matches surface color, color: upper surface; 183B, fading to 187A to 187B at the proximal end, lower surface 146C, strongly tinged 176A.

Inflorescence description:

*Inflorescence type.*—Terminal panicle, comprised of sterile and fertile flowers, fertile flowers are not conspicuous.

*Lastingness of inflorescence.*—Persistent with color lasting from mid-summer to late summer.

*Inflorescence number.*—One per lateral or sublateral stem.

*Inflorescence size.*—Average of 19.3 cm in depth and 15.3 cm in diameter.

*Flower number.*—Average of 700 sterile flowers and 300 fertile flowers per panicle.

*Flower fragrance.*—Faint, sweet and pleasant, typical fragrance for *Hydrangea paniculata*.

*Flower aspect.*—Sterile flowers; upright and outward to slightly drooping, fertile flowers; upright.

*Flower size.*—Sterile flowers; an average of 8 mm in diameter and 4 mm in depth, fertile flowers; an average of 9 mm in diameter and 6 mm in depth.

*Flower type.*—Rotate.

*Flower buds.*—Sterile flowers; average of 4 mm in length and 8 mm in diameter, broadly cup-shaped, ranging between 155A and 158C to 158D in color, fertile flowers; average of 4 mm in length and 3 mm in width, broad obovate in shape, NN155C to NN155D, base 145D and 157A.

*Peduncles.*—Moderately strong, main peduncle (rachis) an average of 14.3 cm in length and 4 mm in width, 185C in color, surface matte, densely covered with thin adpressed hairs, average of 0.5 mm in length, N155A, held in a 60° angle.

*Pedicels.*—Sterile flowers; held at a 40° angle from vertical, an average of 1.7 cm in length and 1 mm in width, moderate strength, NN155A in color, dull, moderately pubescent surface covered with adpressed hairs 0.3 mm in length and NN155A in color, fertile flowers; held in an average angle of 20° to vertical, an average of 2 mm in length and 0.3 mm in diameter, matches color surface, moderate strength, dull, glabrous surface, 157A in color.

*Petals.*—Sterile flowers; single, average of 4, rotate, cruciform in arrangement, narrow ovate in shape, entire margin, acute apex, cuneate base, average of 3 mm in length and 1 mm in width, upper surface smooth, glabrous and very slightly glossy, lower surface smooth, glabrous and matte, color; upper surface when opening and fully open; NN155D, lower surface when opening and fully open; NN155C, fertile flowers; average of 5, rotate, reflexed in arrangement, ovate and moderately concave in shape, an average of 3 mm in length and 1.25 mm width, acute apex, cuneate base, entire margins, very slightly glossy and glabrous on upper and lower surface, upper and lower surface when opening a blend of 155C and 157C, upper and lower surface when fully open 155C, non-fading.

*Sepals.*—Sterile flowers; single, average of 4, occasionally 5, rotate in arrangement, obovate to broadly elliptical in shape, an average of 1.8 cm in length and 1.5 cm width, shallowly retuse to obtuse apex, narrowly cuneate base, entire margins, dull and glabrous on upper and lower surface, color: when opening upper and lower surface 155C, when fully open upper and lower surface a blend of 155C and NN155A, upper surface changing to a blend of 60B and 187D, lower surface changing to 182B, fertile flowers; average of 5, broadly deltoid in shape, entire margin, broad acuminate apex, broad cuneate base, average of 0.75 mm in length and 1 mm in width, smooth and matte on both surfaces, color: when opening and fully open upper surface a blend of 145D and 157A, when opening and fully open lower surface; a blend of 150D and 157A, upper and lower surface fading to 150D in color.

Reproductive organs: (Present on fertile flowers and occasionally on sterile flowers).

*Stamens.*—Sterile flowers; average of 8, anthers broadly oblong in shape, 0.5 mm in length and 155A in color, filaments 2.5 mm in length and 155C in color, pollen is low to moderate in quantity and 156D in color, fertile flowers; average of 10, anthers broadly oblong in shape, 0.4 mm in length and 155C in color, filaments 4 mm in length and 155C in color, pollen is moderate in quantity and 156D in color.

*Pistils.*—Sterile flowers; none present, fertile flowers; average of 2 to 3, an average of 2 mm in length, stigma is club-shaped and 157D in color, style is an average of 1 mm in length and 157A in color, ovary is 157C to 157D in color.

*Fruit and seed.*—Have not been observed to date.

It is claimed:

1. A new and distinct cultivar of *Hydrangea* plant named 'Bokopiav' as herein illustrated and described.

* * * * *